US009820797B2

(12) United States Patent
Burr et al.

(10) Patent No.: US 9,820,797 B2
(45) Date of Patent: *Nov. 21, 2017

(54) CRYOSURGERY SYSTEM

(71) Applicant: CSA Medical, Inc., Lexington, MA (US)

(72) Inventors: Ron Burr, Parkton, MD (US); Rafael Cordero, Bedford, MA (US); Marc Davidson, Andover, MA (US); Wendelin Cherise Maners, Hermosa Beach, CA (US); Janel Petrilli, Pittsburgh, PA (US)

(73) Assignee: CSA Medical, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/869,814

(22) Filed: Sep. 29, 2015

(65) Prior Publication Data

US 2016/0089196 A1 Mar. 31, 2016

Related U.S. Application Data

(63) Continuation of application No. 13/784,596, filed on Mar. 4, 2013, now Pat. No. 9,144,449, which is a
(Continued)

(51) Int. Cl.
*A61B 18/02* (2006.01)
*A61B 18/00* (2006.01)
*A61B 90/00* (2016.01)

(52) U.S. Cl.
CPC ...... *A61B 18/0218* (2013.01); *A61B 2018/00041* (2013.01); *A61B 2018/00577* (2013.01);
(Continued)

(58) Field of Classification Search
USPC .................................................. 606/20–26
See application file for complete search history.

(56) References Cited

U.S. PATENT DOCUMENTS 3,630,203 A 12/1971 Sellinger et al.
3,782,386 A 1/1974 Barger et al.
(Continued)

FOREIGN PATENT DOCUMENTS

JP 53-083380 A 7/1978
JP 2001517475 A 10/2001
(Continued)

OTHER PUBLICATIONS

Non-Final Office Action issued in corresponding Japanese application No. JP2014/560134 dated Dec. 20, 2016.
(Continued)

*Primary Examiner* — Paula J Stice

(57) ABSTRACT

A cryosurgery system for application of medical-grade liquid nitrogen to a treatment area via a small, low pressure, open tipped catheter. The system includes a console, including a touch panel computer, a cryogen module, a suction module and an electronics module, and a disposable spray kit. Features include optional low cryogen flow setting to reduce the cryogen flow rate by 50%, improved cryogen flow consistency reducing pressure pulses and peaks, an integrated suction pump for improved consistency and self-checks, specified vent tube areas and corresponding maximum expected pressures during cryospray procedure; optional pressure sensing capability to monitor pressure during a treatment, and novel catheter designs of multilayer and flexible construction providing a variety of spray patterns.

11 Claims, 18 Drawing Sheets

Related U.S. Application Data continuation-in-part of application No. 13/411,395, filed on Mar. 2, 2012, now Pat. No. 9,301,796.

(52) U.S. Cl.
CPC ............... *A61B 2018/00714* (2013.01); *A61B 2018/00744* (2013.01); *A61B 2018/00761* (2013.01); *A61B 2018/00791* (2013.01); *A61B 2018/00982* (2013.01); *A61B 2018/0212* (2013.01); *A61B 2018/0268* (2013.01); *A61B 2018/0293* (2013.01); *A61B 2090/064* (2016.02); *A61B 2218/003* (2013.01); *A61B 2218/007* (2013.01)

(56) References Cited

U.S. PATENT DOCUMENTS

| | | | |
|---|---|---|---|
| 4,146,030 | A | 3/1979 | Holroyd |
| 5,720,764 | A | 2/1998 | Naderlinger |
| 5,846,235 | A | 12/1998 | Pasricha et al. |
| 6,143,013 | A | 11/2000 | Samson et al. |
| 6,237,355 | B1 | 5/2001 | Li |
| 6,287,304 | B1 * | 9/2001 | Eggers ............... A61B 18/1492 606/37 |
| 6,306,129 | B1 | 10/2001 | Little et al. |
| 6,319,248 | B1 | 11/2001 | Nahon |
| 6,464,716 | B1 | 10/2002 | Dobak, III et al. |
| 6,551,309 | B1 | 4/2003 | LePivert |
| 6,887,234 | B2 | 5/2005 | Abboud et al. |
| 7,331,948 | B2 * | 2/2008 | Skarda ............... A61M 25/0012 604/525 |
| 7,507,233 | B2 | 3/2009 | Littrup et al. |
| 7,785,289 | B2 | 8/2010 | Rios et al. |
| 2002/0143323 | A1 | 10/2002 | Johnston et al. |
| 2004/0024392 | A1 | 2/2004 | Lewis et al. |
| 2005/0081541 | A1 | 4/2005 | Copping |
| 2005/0283136 | A1 | 12/2005 | Skarda |
| 2006/0062895 | A1 | 3/2006 | Pursley |
| 2006/0138177 | A1 | 6/2006 | Wauters et al. |
| 2007/0123852 | A1 | 5/2007 | Deem et al. |
| 2007/0177008 | A1 | 8/2007 | Bayer et al. |
| 2007/0233055 | A1 * | 10/2007 | Abboud ............... A61B 18/02 606/22 |
| 2007/0253463 | A1 | 11/2007 | Perry et al. |
| 2008/0312644 | A1 | 12/2008 | Fourkas et al. |
| 2009/0078875 | A1 | 3/2009 | Rousso et al. |
| 2009/0157002 | A1 * | 6/2009 | Dumot ............... A61B 18/0218 604/131 |
| 2009/0192505 | A1 | 7/2009 | Askew et al. |
| 2010/0057065 | A1 * | 3/2010 | Krimsky ............ A61B 18/0218 606/21 |
| 2010/0057067 | A1 | 3/2010 | Baust et al. |
| 2010/0191232 | A1 | 7/2010 | Boveda |
| 2010/0324483 | A1 | 12/2010 | Rozenberg et al. |
| 2011/0106074 | A1 | 5/2011 | Kunis et al. |
| 2011/0144524 | A1 | 6/2011 | Fish et al. |
| 2011/0208166 | A1 | 8/2011 | Dumot et al. |
| 2013/0110098 | A1 | 5/2013 | Lalonde |
| 2013/0204068 | A1 | 8/2013 | Gnanashanmugam et al. |
| 2013/0218149 | A1 | 8/2013 | Braun et al. |
| 2013/0231651 | A1 | 9/2013 | Burr et al. |
| 2014/0018788 | A1 | 1/2014 | Engelman et al. |
| 2015/0097129 | A1 | 4/2015 | Ben-Ami |
| 2015/0250524 | A1 | 9/2015 | Moriarty et al. |

FOREIGN PATENT DOCUMENTS

| | | |
|---|---|---|
| JP | 2004505664 A | 2/2004 |
| WO | WO9204872 A1 | 4/1992 |
| WO | WO9915093 A1 | 4/1999 |
| WO | WO0211638 A1 | 2/2002 |
| WO | WO2009082433 A2 | 7/2009 |
| WO | WO2009082433 A3 | 10/2009 |
| WO | WO2012006408 A1 | 1/2012 |

OTHER PUBLICATIONS

Supplementary Partial European Search Report issued on (Dec. 19, 2016), for 113877095.3 (5 pages).
Supplementary European Search Report mailed Oct. 19, 2016 in related European application 13754251.0 (6 pages).
Supplementary Partial European Search Report dated (Oct. 19, 2016), for 13754251.0 (4 pages).
International Search Report dated (Mar. 11, 2014), for PCT/US2013/057037 (4 pages).
International Search Report dated Nov. 22, 2013) for PCT/US2013/028935 (4 pages).
T J Lynch, Polyimide Tubing: Dispelling the Myths, Microlumen, http://www.microlumen.com/news/industry-news/18-polyimide-tubing-dispelling-the-myths.

* cited by examiner

| | Round Vent Area | Annular Vent Area |
|---|---|---|
| Diagram of Vent Shape | Vent Tube ID | Vent Tube ID / Annulus / Scope OD |
| Vent Area Calculation | Area ~ 3/4 * $d_{tube}^2$ | Annulus = ½ ($d_{tube}$ - $d_{scope}$) <br> Area ~ 3 * $d_{tube}$ * annulus |

Diagram of Venting Tube Area (d=diameter)

FIG. 7

| Vent Tube ID (mm) | Vent Area (mm²) | Max Pressure (cmH₂O) | |
|---|---|---|---|
| | | Low Flow | Normal Flow |
| 3.2 | 8 | 35 | 95 |
| 5.0 | 20 | 15 | 25 |
| 6.0 | 29 | <15 | <25 |
| 7.0 | 38 | <15 | <25 |

Round Vent Area Calculation and Maximum Expected Pressure during 20sec Cryogen

FIG. 8

| Vent Tube ID (mm) | Scope Outer Diameter (mm) | | | | |
| --- | --- | --- | --- | --- | --- |
|  | 6 | 7 | 8 | 9 | 10 |
| 8.0 | 22 | - | - | - | - |
| 8.5 | 29 | - | - | - | - |
| 9.0 | 36 | 25 | - | - | - |
| 9.5 | 43 | 32 | - | - | - |
| 10.0 | 50 | 40 | 28 | - | - |
| 10.5 | 58 | 48 | 36 | - | - |
| 11.0 | 67 | 57 | 45 | 31 | - |
| 11.5 | 76 | 65 | 54 | 40 | - |
| 12.0 | 84 | 75 | 63 | 50 | 35 |
| 12.5 | 94 | 84 | 72 | 59 | 44 |

Annular Vent Area Calculation (mm²)

FIG. 9

| Vent Area (mm²) | Max Pressures (cmH$_2$O) | |
| --- | --- | --- |
|  | Low Flow | Normal Flow |
| 8 | 60 | 125 |
| 20 | 25 | 40 |

Annular Vent Area Maximum Expected Pressure during 20sec Cryogen

FIG. 10

Lumped Parameter Schematic for Cryospray System Tuning and Control

CRYOSURGERY SYSTEM

BACKGROUND

1. Field of the Invention

The present invention relates generally to cryospray systems, cryogenic spray ablation and cryosurgery systems, and more particularly, to an advanced cryospray ablation system having consistent cryogen flow and flow control, an integrated suction pump, a body cavity pressure sensor and an assortment of flexible cryogen delivery catheters.

2. Related Art

A variety of medical conditions may be treated by ablation of tissue within the body. Tissue ablation refers to the removal or destruction of tissue, or of tissue functions. Traditionally, invasive surgical procedures were required to perform tissue ablation. These surgical procedures required the cutting and/or destruction of tissue positioned between the exterior of the body and the site where the ablation treatment was conducted, referred to as the treatment site. Such conventional surgical procedures were slow, costly, high risk, and resulted in a long recovery time.

Cryoablation is a relatively new procedure in which tissue ablation is conducted by freezing diseased, damaged or otherwise unwanted tissue (collectively referred to herein as "target tissue"). Appropriate target tissue may include, for example, cancerous or precancerous lesions, tumors (malignant or benign), fibroses and any other healthy or diseased tissue for which cryoablation is desired.

Cryoablation may be performed by using a system that sprays low pressure cryogen on the target tissue. Such systems are often referred to as cryospray systems, cryosurgery spray systems, cryosurgery systems, cryogen spray ablation systems or simply cryospray ablation systems. As used typically, cryogen refers to any fluid (e.g., gas, liquefied gas or other fluid known to one of ordinary skill in the art) that has a sufficiently low boiling point to allow for therapeutically effective cryotherapy and is otherwise suitable for cryogenic surgical procedures. For example, acceptable fluids may have a boiling point below approximately negative (−) 150° C. The cryogen may be nitrogen, as it is readily available. Other fluids such as argon and air may also be used. Additionally, liquid helium, liquid oxygen, liquid nitrous oxide and other cryogens can also be used.

During operation of a cryosurgery system, a clinician, physician, surgeon, technician, or other operator (collectively referred to as "operator" herein), sprays cryogen on the target tissue via a delivery catheter. The spray of cryogen causes the target tissue to freeze or "cyrofrost." This freezing of the tissue often causes the target tissue to acquire a white color (indicative of cryofrost). The white color indicates that the target tissue freezing has initiated. The physician may visually monitor and/or time additional cryospray duration in order to control the depth of injury. The temperature range for cryofrost can be approximately negative (−) 10° C. to approximately negative (−) 75° C. Alternatively, the temperature range can be from negative (−) 50° C. to (−) 195° C., particularly in the case of liquid nitrogen at low pressure. However, the particular temperature for cryofrost will depend on the target tissue, including size, location, etc. The time period to reach cryofrost may vary, from approximately 5 seconds to approximately 2 minutes or more depending on the size and location of the target tissue and the thermodynamic potential of the cryogen. A cryosurgery system may include a camera system that enables the operator to monitor the cryogen delivery and determine when cyrofost has occurred.

SUMMARY OF THE INVENTION

According to one aspect of the present invention, there is provided an advanced cryosurgery system having improved cryogen flow and flow control, an integrated suction pump, a pressure sensor and an improved delivery catheter.

Embodiments of the present invention are directed to a cryospray system having a cryogen delivery apparatus. In accordance with embodiments of the present invention, the cryospray ablation system may further include a cryogen source configured to provide the cryogen to the cryogen delivery apparatus, a regulation apparatus fluidically coupled to the cryogen source and to the cryogen delivery apparatus, and a controller communicatively coupled to the regulation apparatus configured to control the release of cryogen into the cryogen delivery apparatus. Exemplary cryosurgery systems in which the present invention may be implemented include, but are not limited to, those systems described in commonly owned U.S. Pat. Nos. 7,255,693, 7,025,762, 6,383,181, and 6,027,499 and U.S. patent application Ser. Nos. 11/956,890 and 12/022,013, the entirety of which are each hereby incorporated by reference herein. Embodiments of the present invention are described below in connection with one embodiment of such exemplary cryosurgery system shown in FIG. 1.

The system of the present invention is a cryosurgical tool that applies a medical-grade liquid nitrogen spray to the treatment area via a small, low pressure, open tipped catheter. The system of the present invention may optionally include one or more of (1) a console, including a touch panel computer, a cryogen module, a suction module and an electronics module, all packaged in a mobile cart, and (2) a disposable spray kit.

According to one embodiment, users interact with the console through a dual foot pedal and the touch panel. A processor/controller and associated software manage the cryogen level sensing, filling, pressure, cooling, defrost, suction, timing and/or data management functions. A wireless remote control may provide alternative timer control from a distance in the treatment room. A fill kit, stored on the rear of the console, in conjunction with software controls, may allow for semi-automatic liquid nitrogen transfer from the source tank to the console. Safety features may include sensors, indicators, tank pressure relief valves, an isolated low voltage power system, and an emergency button to be used in the event of user or technical malfunction. The system may optionally be mounted on or in a mechanical cart for easy maneuvering. The mechanical cart may have on-board storage built into the panels for the foot pedals, instructional material (e.g. operator manual), disposables (e.g., spray kits), remote control and fill kit. Modular design of the console may allow for easy manufacturability and serviceability.

According to another embodiment, users may optionally interact with a actuator button or trigger in the catheter body that allows for engaging additional control valves or orifices which allow for flow of the cryogen spray onto the treatment site.

According to another embodiment, a spray kit of the present invention may include a sterile, single-use flexible catheter a cryogen decompression tube, and pre-cut accessory suction tubes. The catheter is flexible and capable of retroflex in a scope. The cryogen decompression tube and other accessory tubes are included for use with the on-board suction system.

In particular, several key features may be added for optimal cryogen flow/delivery and gas venting:

- optional low cryogen flow setting to reduce the cryogen flow rate by 50%,
- cryogen flow consistency that helps reduce pressure pulses and peaks (through sensors, control systems, and control algorithms),
- an integrated suction pump for improved consistency and self-checks,
- specified vent tube areas and corresponding maximum expected pressures during cryospray procedure;
- optional pressure sensing capability to monitor body cavity pressure during a treatment, and
- catheter designed to be retroflex capable.

As a result of the novel cryogen delivery features, the cryogen flow delivers a consistent flow with minimal pressure pulsing to create an efficient cryogen flow which generates low pressure in the body. As a result of the gas venting features, the active suction delivers consistent venting and has settings and warnings that provide greater flexibility to the physician. The addition of passive venting instructions provides information regarding cryogen flow and vent area so that the physician can make an informed decision on the appropriate combinations to limit pressure build-up within a body cavity. In addition, an optional pressure sensing capability is available to monitor pressure during a treatment.

BRIEF DESCRIPTION OF THE DRAWINGS

Embodiments of the present invention will be described in conjunction with the accompanying drawings, in which:

FIG. 7 is a diagram of venting tube area;

FIG. 8 shows round vent area calculation and maximum expected pressure during 20 sec cryosurgery.

FIG. 9 shows annular vent area calculation.

FIG. 10 shows annular vent area maximum expected pressure during 20 sec. cryosurgery.

DETAILED DESCRIPTION OF THE PREFERRED EMBODIMENTS

Figure 1:
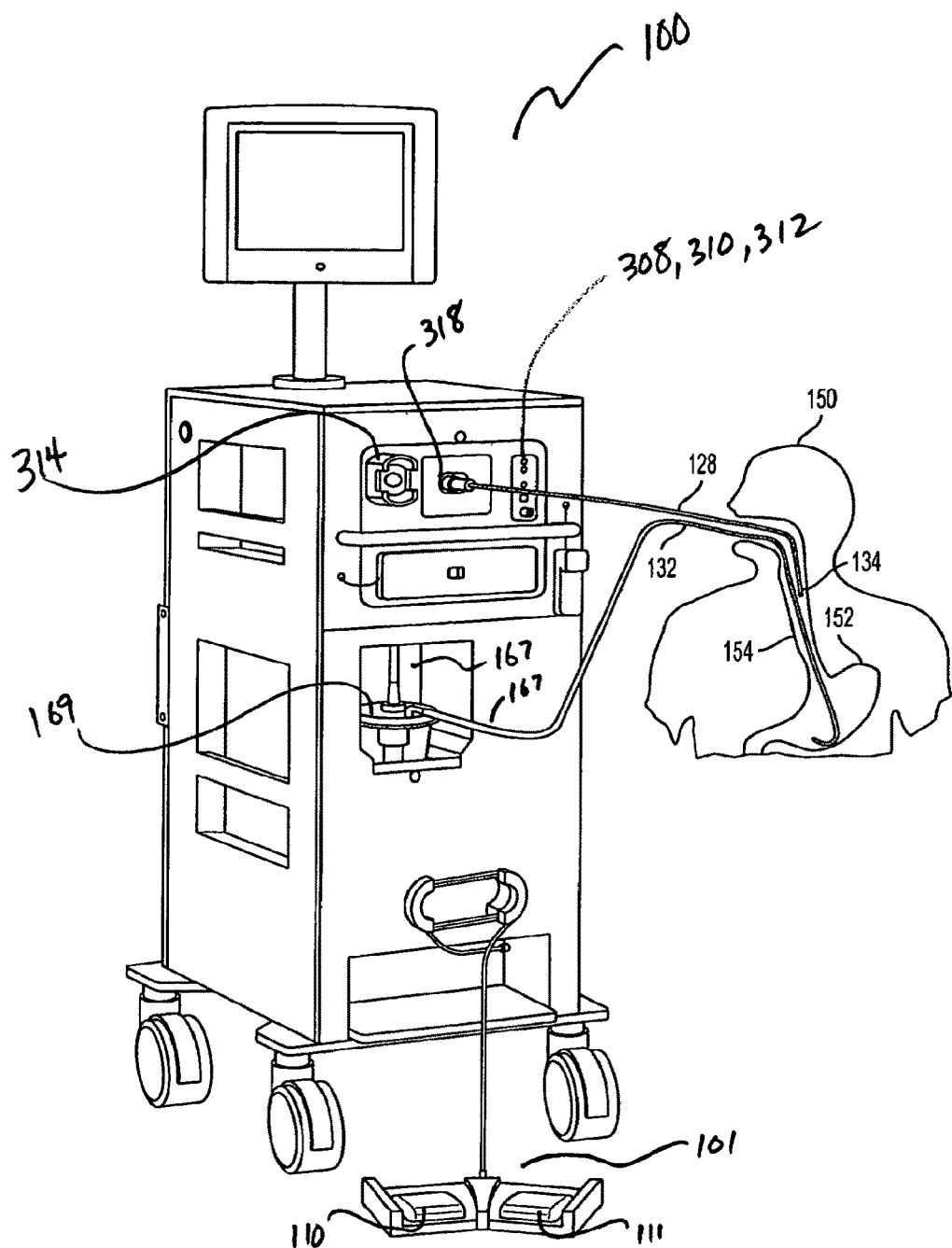
FIG. 1 is a perspective view of a cryosurgery system according to an embodiment of the invention.
Figure 2:
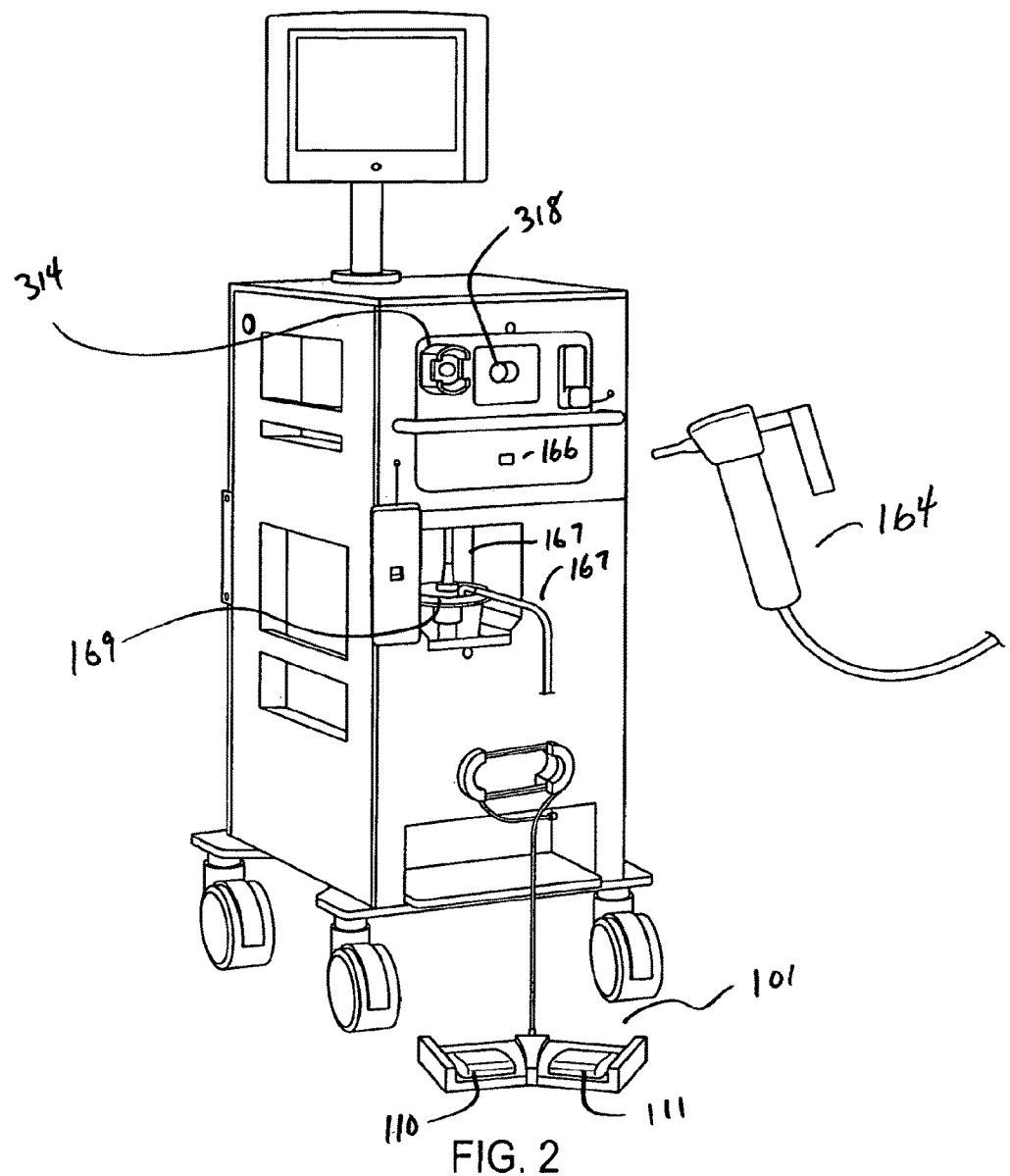
FIG. 2 is a perspective view of another embodiment of a cryosurgery system according to an embodiment of the invention.
Figure 3:
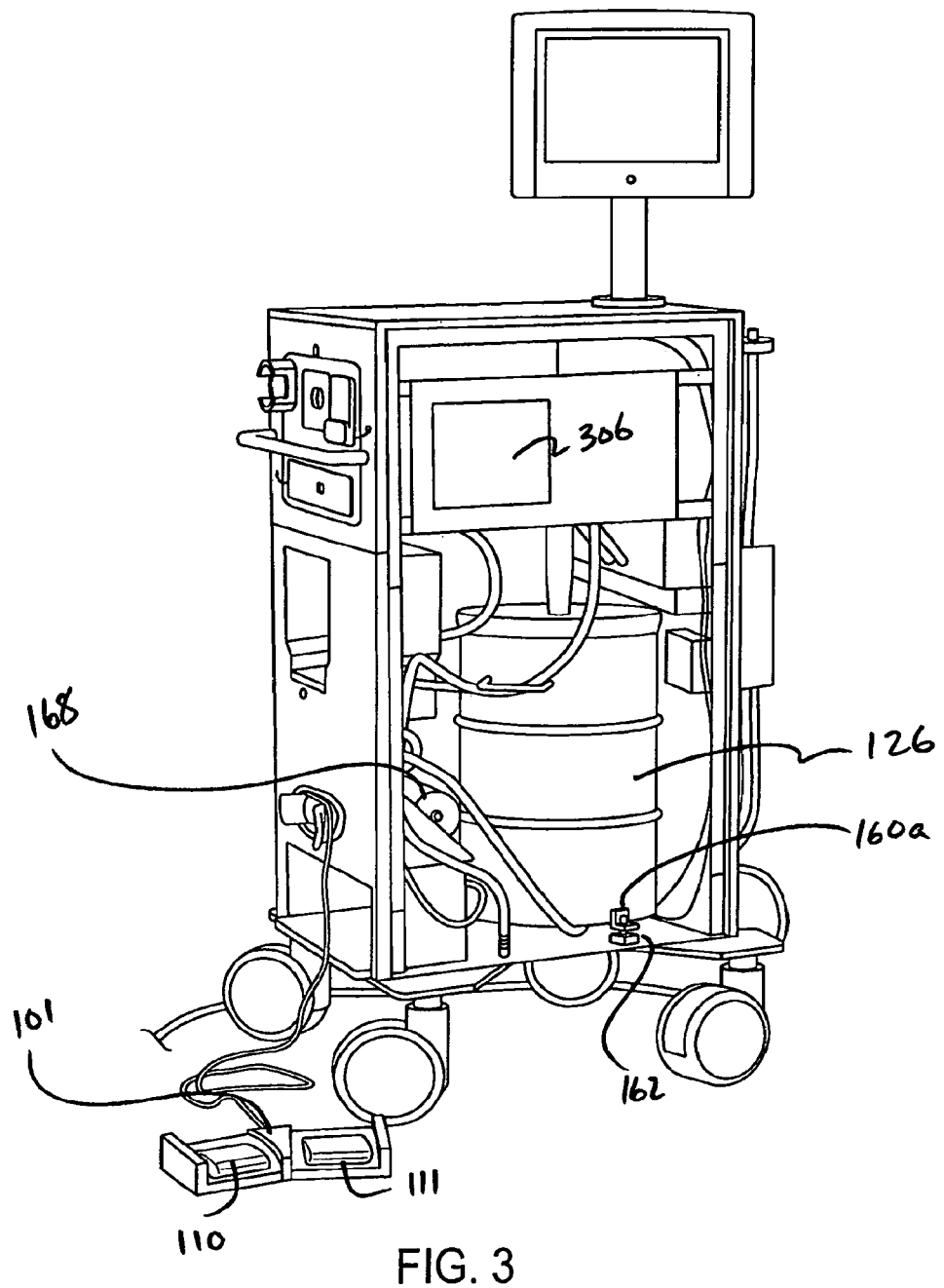
FIG. 3 is a perspective view of the interior of an embodiment of a cryosurgery system according to an embodiment of the invention.

A simplified perspective view of an exemplary cryosurgery system in which embodiments of the present invention may be implemented is illustrated in FIGS. 1-3. Cryosurgery system 100 comprises a pressurized cryogen storage tank 126 to store cryogen under pressure. In the following description, the cryogen stored in tank 126 is liquid nitrogen although cryogen may be other materials as described in detail below. The pressure for the liquefied gas in the tank may range from 5 psi to 50 psi. According to a more preferred embodiment, pressuring in the tank during storage is 40 psi or less, and pressure in the tank during operation is 35 psi or less. According to a more preferred embodiment, pressure in the tank during storage is 35 psi or less and pressuring during operation is 25 psi or less. According to a most preferred embodiment, pressure during operation at normal nitrogen flow is 22±2 psi, and pressure during operation at low nitrogen flow is 14±2 psi. When the pressure in the tank during operation is set to 22 psi, the flow rate/cooling capacity of the nitrogen is 25 W. When the pressure in the tank during operation is set to 14 psi, the flow rate/cooling capacity of the nitrogen is 12.5 W. In an alternate embodiment, the cryogen pressure may be controlled all the way to 45 PSI and to deliver through smaller lumen catheters and additional feature sets. In such alternate embodiments the pressure in the tank during storage may be 55 psi or less. For the purpose of this application, the term low pressure means 2 psi to 18 psi, preferably 6 psi to 15 psi.

Level and Fill

Liquid nitrogen (LN2) resides on the bottom of the tank and liquid nitrogen gas/vapor (GN2) occupies the top portion of the tank. The tank is supported at three points, 160a, 160b, 160c; see FIGS. 3 and 4. The tank level is measured with a precision load cell 162 under a flange built into the front mount of the cryogen tank and acting of one of the three support points. The load cell effectively measures a portion of the tank's weight, which increases linearly with nitrogen content. Typically, the load cell senses the ⅓ of the weight of the tank. A signal conditioner amplifies the signal for input to an analog input channel of the controller, which is read by the software and used to determine/display the actual tank level. This system provides improved level of precision for monitoring the tank level than conventional tank weight monitoring systems that rely on spring load systems. In an alternate embodiment, tank level is monitored electronically via a sensor internal to the tank that changes value with the level of the liquid inside the tank. This can be done in a variety of ways, including but not limited to capacitively (an example being a Rotarex C-Stic), resistively, or by measuring differential pressure.

The console of the present invention comes with an insulated quick release custom fill hose 164 to fill the tank through the external fill port 166 in a semi-automatic cryogen fill process. A fill port switch 168 on the console actuates only when the fill hose is in the locked position. During the fill process, liquid nitrogen passes through a filter 170 and transfer valve 172 en route to the tank; see FIG. 5. The software automatically shuts off the electronic transfer valve 172 when the tank is full and vents the hose prior to removing from the console. According to an alternate embodiment, manual filling can take place by mechanically bypassing the electronic transfer and vent valves with manual valves, thus allowing the tank to be filled without the need for computer control.

Pressure

The system of the present invention utilizes valves and a pressure transducer to continuously monitor and control the pressure of liquid nitrogen in the tank during use. The console monitors the current pressure of the tank via a pressure transducer 174. The software reads the current pressure from the transducer and adjusts the pressure accordingly. If pressure is too low, the software actuates the pressure build circuit valve 176 to increase the pressure to a specified threshold and then turns off. When the pressure is too high, the software turns on the vent valve 178 until the pressure reaches a specified threshold. According to one embodiment, the system allows two user selectable pressure levels (corresponding to two nitrogen flow rates), normal (24±2 psi/25 W) and low (12±2 psi/12.5 W). According to other embodiments, the system may have selectable pressure levels of 22±2 psi/25 W) and low (14±2 psi/12.5 W). Other embodiments may have ranges of normal pressure from 20 to 30 psi (16 to 30 W) and 30 to 55 psi. The console of the present invention may have a redundant pressure switch 180 designed to confirm and ensure accurate tank pressure readings. According to alternate embodiments, the system of the invention may have a selectable low pressure level from one quarter to three quarters of the normal pressure setting. In an alternate embodiment the flow is not achieved via a pressure setting, but instead via a feature in the catheter that controls the output flow and pressure at its distal end by the use of a nozzle or length of catheter that adjusts the flow utilizing the Pouiselle effect relating to the radius of the pipe that fluid is flowing through. Such embodiment then may utilize the RFID tag in the console to help identify, set up and report flow rates, fluid amount monitoring, and catheter type and type of flow (such as low) been given by such accessory.

A mechanical relief valve 182 on the console tank ensures that the tank pressure stays in a safe pressure range. Constant pressure monitoring and adjustment, allows the set point on the mechanical relief valve to be set at 35 psi, allowing for a low tank storage pressure. A redundant burst disk 184 provides protection should the mechanical relief valve fail. For optimal safety, both electronic and mechanical pressure valves are present to regulate the pressure, providing triple redundancy in the event of failure. In addition, a redundant pressure switch was designed into the system to provide accurate tank pressure readings and is checked during the built-in-test (BIT). In an alternate embodiment, the mechanical relief valve may be set at 60 psi, but still allowing to remain a low pressure storage tank.

Thermal Cooling

The system of the present invention utilizes a manifold assembly comprised of a cryogen valve 186, catheter valve 188, and defrost valve 190 to control liquid nitrogen delivered through the catheter. When the cryogen valve 186 is actuated, liquid nitrogen exits the tank through the lance 194 and proceeds through the manifold assembly 196 where an orifice is present to allow cold expanded gas and liquid cryogen to exit the line through a vent 192 or other fixed orifice and cool down the internal cryogen circuit. During this precool, the catheter valve 188 downstream of the manifold remains closed. A data acquisition board collects data from a thermocouple located on the manifold body. In the precool function, the system software monitors data from the thermocouple, and opens the cryogen valve to cool the manifold when its temperature is above the desired set-point. In an alternate embodiment, when the cryogen valve 186 is actuated, liquid nitrogen exits the tank through the lance 194 and proceeds through the manifold assembly 196 where an in-line orifice is present to allow cold expanded gas and liquid cryogen to exit, which will in turn allow for gas to travel through a length of pipe or coil that will aid in the warming and total expansion of the such gas-liquid mix. This action of allowing the cryogen to escape through the inline orifice precools the pipeline all the way to the gas expansion junction. A thermocouple mounted at that junction monitors to the desired temperature and acts as one of the control variables. In an alternate embodiment, the cold expanded gas-liquid cryogen mix flows through other parts of the cooling circuit to precool additional components before exiting the system. In yet another embodiment, the cold expanded gas-liquid cryogen mix is collected in an insulated collection vessel rather than exiting the system. Pressure in the collection vessel is monitored and controlled in a way similar to that of the main cryogen tank. Pressure in the collection vessel is preferably maintained at a pressure lower than that at the exit point of the venting in-line orifice. Periodically, the controlling system will transfer collected cryogen from the collection vessel back to the primary cryogen tank by pressurizing the collection vessel to a pressure higher than that of the primary cryogen tank. This action may also include venting the primary cryogen tank to reduce pressure, thereby increasing the pressure differential. Once a sufficient pressure differential is achieved, the transfer valve is then opened allowing cryogen to flow from the collection vessel back into the primary cryogen tank. Upon completion of transfer, the controlling system closes the transfer valve and returns pressures back to their respective operating levels. The collection vessel may be a separate standalone tank, or integrated into the primary cryogen tank.

Depressing the cryogen foot pedal 110 opens both the cryogen valve 186 and catheter valve 188 allowing liquid nitrogen to flow into the catheter 128; releasing the pedal stops the flow of cryogen (momentary action). The software set-up screen provides two user selectable cooling levels of cryogen flow, normal and low, described above. Nominal cooling performance at normal and low flow is 25 W and 12 W, respectively. In an alternate embodiment as the two phase flow travels past the catheter valve 188, it may encounter a second manifold or pipe section with an orifice to allow for expanded gas to vent and divert it away from the catheter input. In yet another embodiment the two phase flow may encounter a junction assembly that acts as gas separator by allowing any gas expansion to exit via an in-line orifice in the pipeline which will in turn allow for gas to travel through a length of pipe or coil that will aid in the warming and total expansion of the such vented gas. The vented gas is then allowed to vent to atmosphere safely. In the embodiment, the inline orifice may be made of stainless, or brass. In an alternate embodiment, this orifice is made of ruby, sapphire or corundum. The use of this material allows for precise control of the orifice size as well as for the use of very small hole sizes such as 0.020", 0.038", or within a range of sizes from 0.010" to 0.075".

Low cryogen flow generates considerably less pressure rise with the same venting area and allows treatment with more precise control. The precooling process has been automated on the console of the present invention where the prior art console requires the physician to manually spray prior to inserting into the scope. Automated precool with internal circulation (improved over manual flow through catheter) allows improved ease of use and maximizes cooling consistency and minimizes gas discharged into patient.

In the embodiment illustrated in FIG. 1, a conventional therapeutic endoscope 134 is used to deliver the nitrogen gas to target tissue within the patient. Endoscope 134 may be of any size, although a smaller diagnostic endoscope is preferably used from the standpoint of patient comfort. In certain embodiments, a specially designed endoscope having a camera integrated therein may also be used. As is known, an image received at the lens on the distal end of the camera integrated into endoscope 134 may be transferred via fiber optics to a monitoring camera which sends video signals via a cable to the a conventional monitor or microscope, where the procedure can be visualized. By virtue of this visualization, the surgeon is able to perform the cryosurgery at treatment site 154.

As the liquid nitrogen travels from tank 126 to the proximal end of cryogen delivery catheter 128, the liquid is warmed and starts to boil, resulting in cool gas emerging from the distal end or tip of catheter 128. The amount of boiling in catheter 128 depends on the mass and thermal capacity of catheter 128. Since catheter 128 is of small diameter and mass, the amount of boiling is not great. (The catheter would preferably be of size seven French.) When the liquid nitrogen undergoes phase change from liquid to gaseous nitrogen, additional pressure is created throughout the length of catheter 128. This is especially true at the solenoid/catheter junction, where the diameter of the supply tube to the lumen of catheter 128 decreases from approximately 0.25 inches to approximately 0.070 inches, respectively. But the catheter range diameter of its lumen may be between 0.030 to 0.100 inches. In an alternate embodiment the gas boiling inside the catheter may be reduced even greater by the use of insulating materials such as PTFE, FEP, PEBAX® and others to help reduce its temperature coefficient. The addition of PTFE is especially desirable if done in the inner lumen because its lower coefficient of friction aids in laminar flow of the fluid and thus reducing turbulence and entropy. This reduces gas expansion and allows for good fluid velocity.

Figure 23:
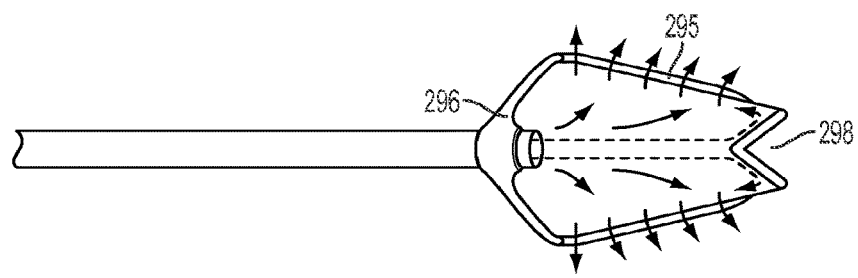
FIG. 23 shows an internal cross-section of a diffuser element according to the invention.
Figure 24:
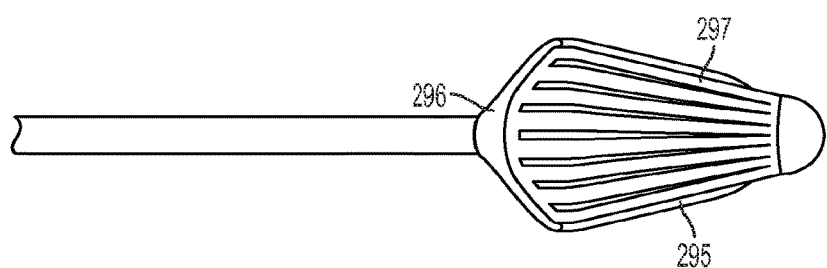
FIG. 24 shows an external side view of a diffuser element according to the invention

When the liquid nitrogen reaches the distal end of catheter 128 it is sprayed out of cryogen delivery catheter 128 onto the target tissue. It should be appreciated that certain embodiments the cryosurgery system may be able to sufficiently freeze the target tissue without actual liquid nitrogen being sprayed from catheter 128. In particular, a spray of liquid may not be needed if cold nitrogen gas is capable of freezing the target tissue. When the catheter sprays out of the catheter distal tip it is described as straight spray. In the alternate embodiment illustrated in FIG. 24 the liquid nitrogen may be broken down into small droplets via a diffuser 295 or filter to allow for a very even spray pattern and avoid cold spots of spray pattern. The diffuser 295 may be constructed of filter paper, a grating patterned polymer, a metal or plastic mesh basket or laser cutting methods on the shaft itself to pattern it with very small holes. In such embodiment, the catheter ends in a cap 296 that contains small longitudinal cuts 297 that provide for controlled spray to exit as it initially hits a bounce plate 298 on FIG. 23. The bounce plate 298 is of a conical shape and helps distribute the spray evenly all around the diffuser 295 and cap 296

Freezing of the target tissue is apparent to the physician by the acquisition of a white color, referred to as cryofrost, by the target tissue. The white color, resulting from surface frost, indicates the onset of mucosal or other tissue freezing sufficient to initiate destruction of the diseased or abnormal tissue. The operator may use the system timer to freeze for a specified duration once initial cryofrost is achieved in order to control the depth of injury. In one embodiment, the composition of catheter 128 or the degree of insulating capacity thereof will be selected so as to allow the freezing of the tissue to be slow enough to allow the physician to observe the degree of freezing and to stop the spray as soon as the surface achieves the desired whiteness of color. The operator may monitor the target tissue to determine when cryofrost has occurred via the camera integrated into endoscope 134. The operator manipulates cryogen catheter 128 to freeze the target tissue. Once the operation is complete, cryodecompression tube 132, catheter 128, and endoscope 134 are withdrawn.

Figure 11:
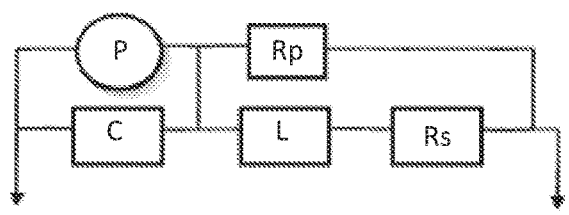
FIG. 11 shows schematic diagram of cryogen flow path and fluidic tuning and control to achieve consistent and stable flow and cooling.
Figure 12:
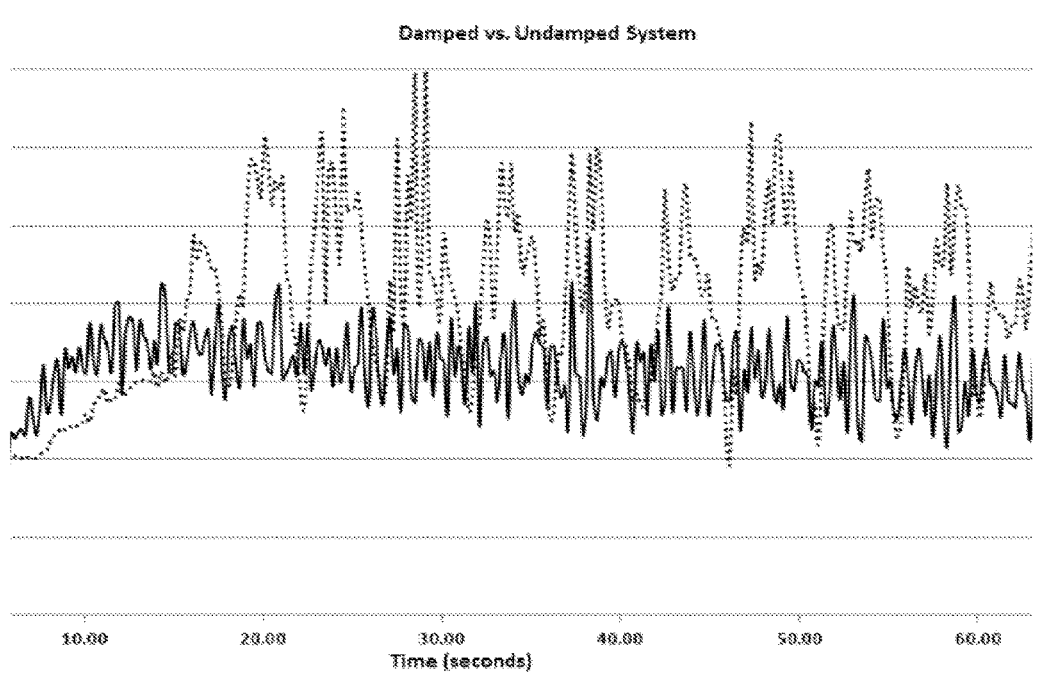
FIG. 12 shows typical pressure response of a "damped" cryogen system with 'critical damping' indicating minimal overshoot and low peak body cavity pressure versus an "undamped" system.

Proper design and matching of cryogen storage and control components allows for stable and well-controlled cryogen flow. The dynamic behavior of the system can be simply visualized by the lumped parameter model of FIG. 11, where P represents the pressure in the tank; $R_p$ represents "parallel resistance" which models the resistance of the vent orifice 192; C represents the fluid compliance capacity (i.e., the compressibility or "springiness" of the liquid and gas in the tank 126, together with the tank level head height); $R_s$ represents the series resistance, or the length and inside diameter of the catheter; and I represents Inductance, or the weight of the long narrow fluid column in the catheter. The inventors have discovered a critical intersection of these values that provides an ideal and critically damped response to the cryogen and subsequent gas flow/pressure allowing dramatically improved smoothness and consistency of cryogen delivery to the target tissue as compared to the prior art, as shown in FIG. 12.

Catheter length may be anywhere from 10 inches to 100 inches. Inside diameter of the catheter may be anywhere from 0.8 mm to 5 mm, preferably from 1 mm to 4 mm. The tank size may be anywhere from 5 L to 100 L; its diameter may range from 4 inches to 36 inches. The vent orifice of the manifold may be 0.01 inches to 0.1 inches. The inventors have discovered that the following critical combination of dimensions provides a surprisingly improved smoothness and consistency of cryogen delivery: catheter length: 84 inches; catheter inside diameter: 0.07 inches; tank size: 17 L; tank diameter: 12 inches; manifold vent orifice: 0.05 inches. In an alternate construction the catheter length may be 75 inches with a catheter inside diameter of 0.055 inches; tank size of 28 L; tank diameter: 14 inches; cryogen valve gas junction vent orifice of 0.038 inches and catheter valve gas junction vent orifice of 0.020 inches.

Active feedback control via pressure, resistance or bypass control and also be incorporated to aid in ideal tuning and response.

Thermal Defrost

The defrost function is useful for thawing the catheter after cryogen spray, before removal from the scope. A defrost circuit directs gaseous nitrogen from the top of the tank through a heater 191 and defrost valve 190 to the catheter 128. When the defrost button on the software screen is pressed, the defrost circuit is activated for a prescribed time (e.g. 30 seconds) but can be stopped earlier at the user's discretion. A low voltage (24 VDC) DC defrost heater delivers 6W minimum of warming/defrost performance but minimizes variation due to line voltage and limits maximum gas temperature, as compared to the prior art line voltage (120V) AC heater.

Figure 6:
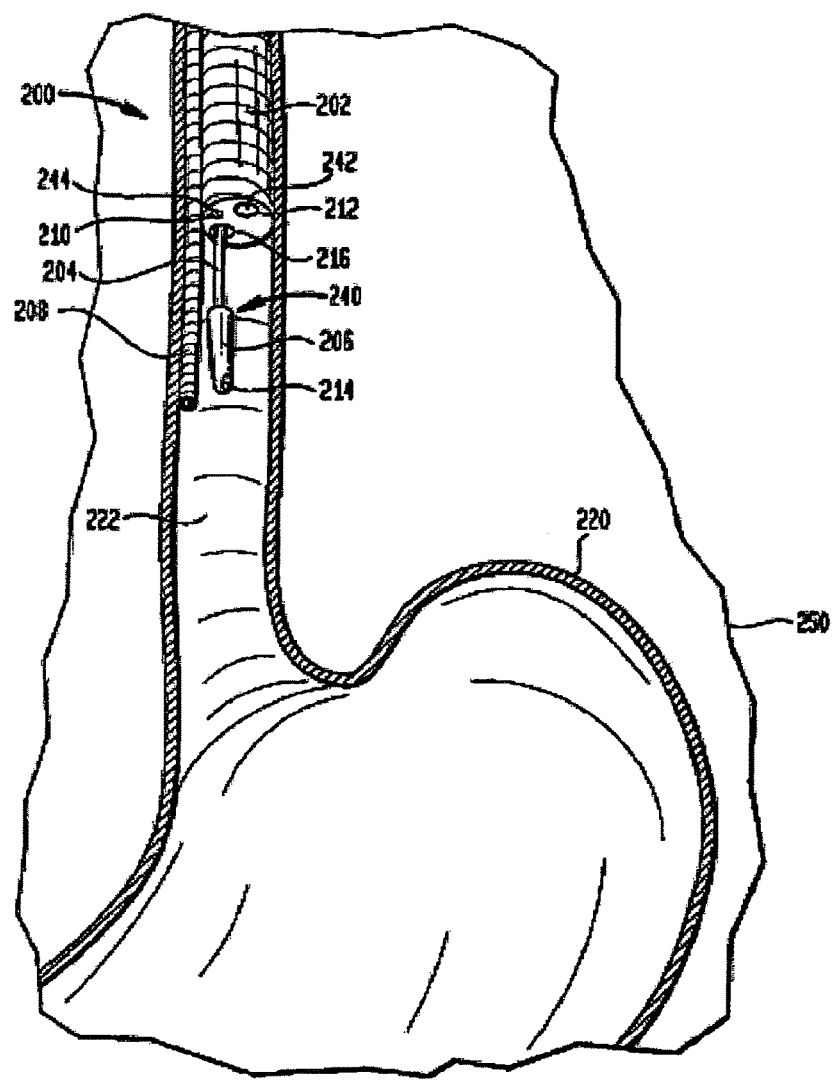
FIG. 6 is a perspective view of a crysurgery delivery system according to an embodiment of the invention.

FIG. 6 is a perspective view of a portion of a cryosurgery system 200 having a cryogen delivery apparatus 240. Cryosurgery system 200 comprises an endoscope 202 having lumens 210, 212 and 216 therein. As shown, endoscope 200 may be positioned in the esophagus 222 of patient 250. Lumen 212, disposed in endoscope 202, is configured to receive an endoscope camera 242. An image received at the lens of endoscope camera 242 may be transferred via fiber optics to a monitoring camera. The monitoring camera then sends video signals via a cable to a conventional monitor or microscope, where the image captured by the lens can be visualized. As shown in FIG. 6, endoscope camera 242 may be inserted through lumen 212 to allow an operator to view the cryosurgery procedure. Lumen 210 is configured to have disposed therein a light 244 that is configured to illuminate the treatment site.

Lumen 216 is configured to receive cryogen delivery apparatus 240. Cryogen delivery apparatus 240 comprises a retroflex-capable cryogen delivery catheter 204, catheter tip 206, and one or more holes 214. After insertion of the cryogen delivery apparatus into the patient, cryogen is provided to cryogen delivery catheter 204 from a cryogen source. Tip 206 causes the cryogen to be sprayed on the target tissue via hole 214. A dual lumen (for both passive and active venting) cryodecompression tube 208 is provided to evacuate the treatment area of undesirable gases, particles, fluids etc Treatment site 154 as depicted in FIG. 1 is the esophagus of patient 150. It should be appreciated, however, that the treatment site but may be any location within patient 150 such as inside stomach 152 or other cavities, crevices, vessels, etc. Since freezing is accomplished by boiling liquid nitrogen, large volumes of this gas are generated. This gas must be allowed to escape. The local pressure will be higher than atmospheric pressure since the gas cannot easily flow out of the treatment site such as the gastrointestinal tract. In the illustrated embodiment, nitrogen gas will tend to enter stomach 152, which has a junction with the esophagus (the esophageal sphincter) immediately adjacent to treatment site 154. In this case, without adequate or quick suction, stomach 152 of patient 150 may become distended and become uncomfortable for patient 150. This buildup of gas could also potentially cause stomach 152 or its lining to become damaged or torn. As such, to prevent this buildup of gas in stomach 152, a suction tube 132 (e.g., a nasogastric tube) as described hereinafter may be inserted into the patient to evacuate cryogen and other gases, particles, liquids, etc. from the patient.

Passive Venting

Passive venting is a method in which gas disperses from the treatment area by flow through either a natural or artificial orifice/lumen without suction. The instructions for use provide physicians with information on passive venting (cryogen flow, vent area, vent shape, see FIGS. 3-6) to limit pressure build-up in the body cavity. The area through which gas vents passively must be adequate to ensure excessive distention does not occur (e.g. 20 mm$^2$ at normal flow and 10 mm$^2$ at low flow). An optional (auxiliary) pressure sensing capability is built-in to aid the user in monitoring cavity pressure, if desired in either the active or passive venting modes.

The operating instructions allow physicians to determine the appropriate cryogen flow setting, vent area and vent shape (round, annular) to utilize passive venting. In addition, the smooth and consistent cryogen spray allows for the reduction of pressure/pulsing by 50% at normal flow settings on the system of the present invention as compared to the prior art. With the low cryogen flow setting, the pressure is significantly reduced even further. Additionally, the console of the present invention has a pressure sense capability that can be used in conjunction with passive venting that allows the physicians to monitor cavity pressure during treatment.

Figure 4:
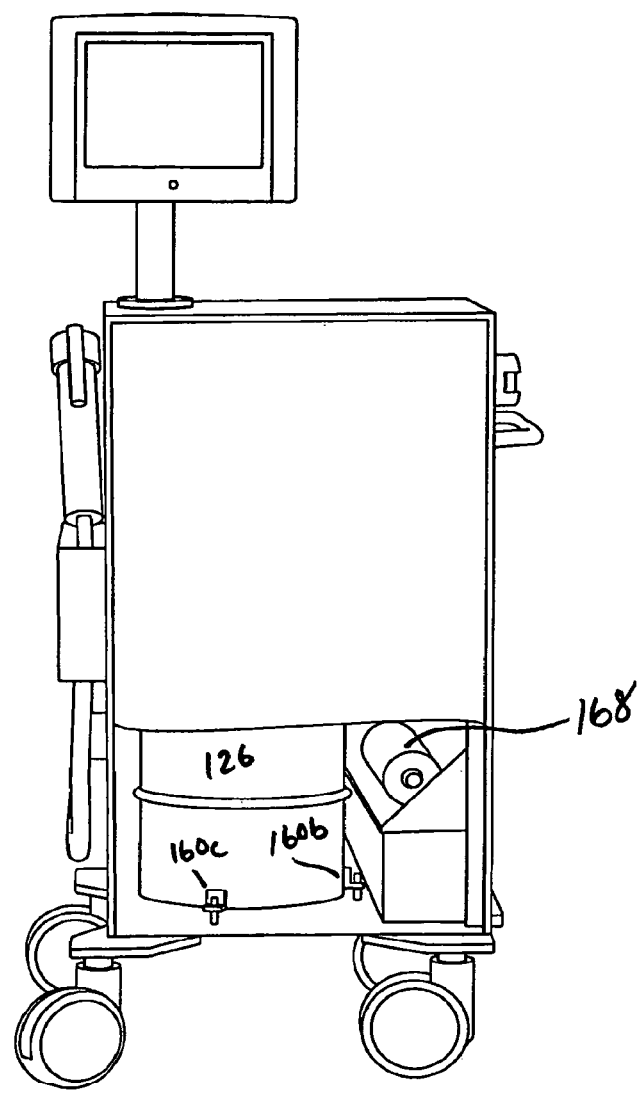
FIG. 4 is a perspective cutaway view of the reverse side of the embodiment of a cryosurgery system shown in FIG. 3.
Figure 5:
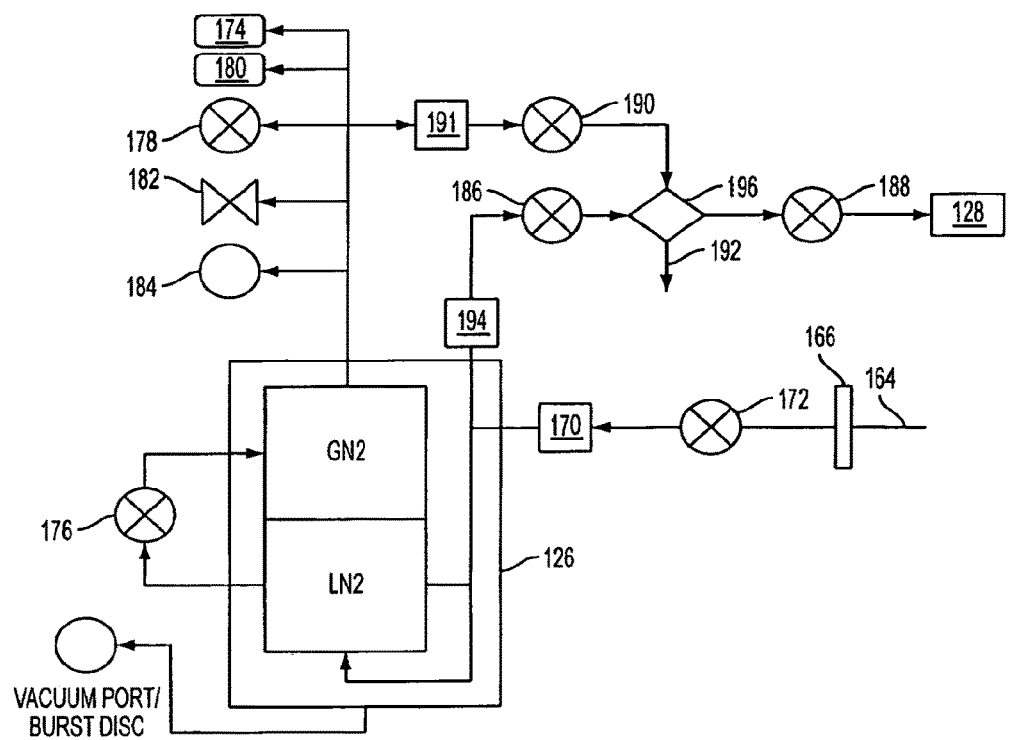
FIG. 5 is a schematic showing a cryogen storage, delivery and pressure control apparatus according to an embodiment of the invention.
Figure 13:
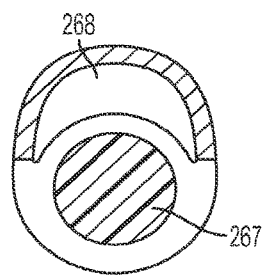
FIG. 13 shows front view of a vent tube according to one embodiment of the invention.
Figure 14:
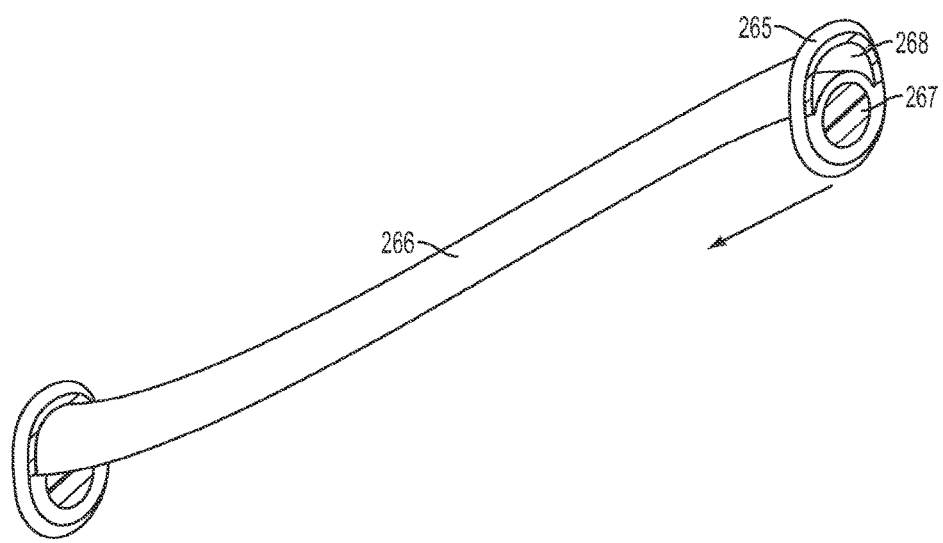
FIG. 14 is a perspective side view of the vent tube shown in FIG. 13.
Figure 15:
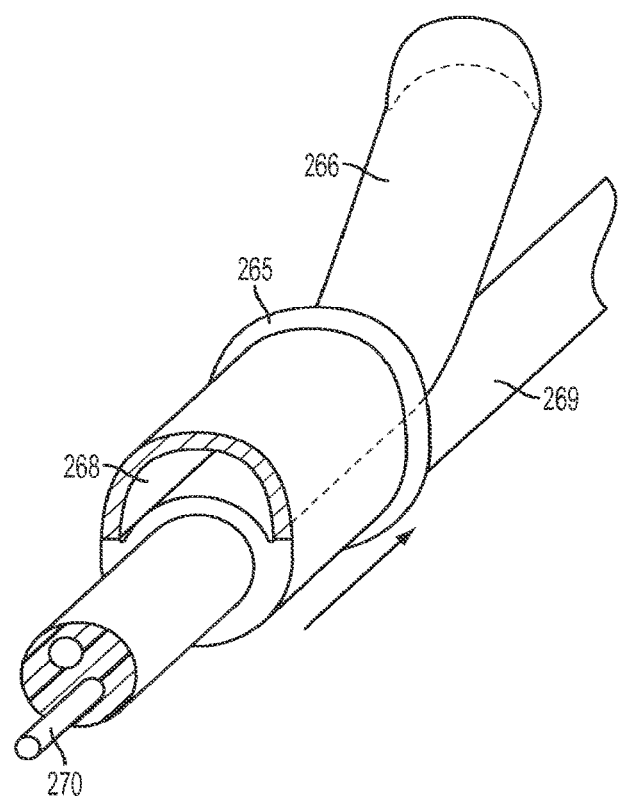
FIG. 15 is a perspective view of the vent tube shown in FIGS. 13 and 14, mated with a scope.
Figure 16:
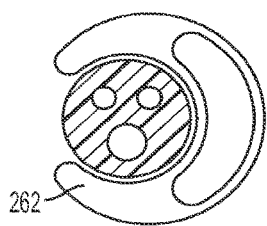
FIG. 16 is a front view of a vent tube according to another embodiment of the invention, together with the front face of a scope with which it is mated.
Figure 17:
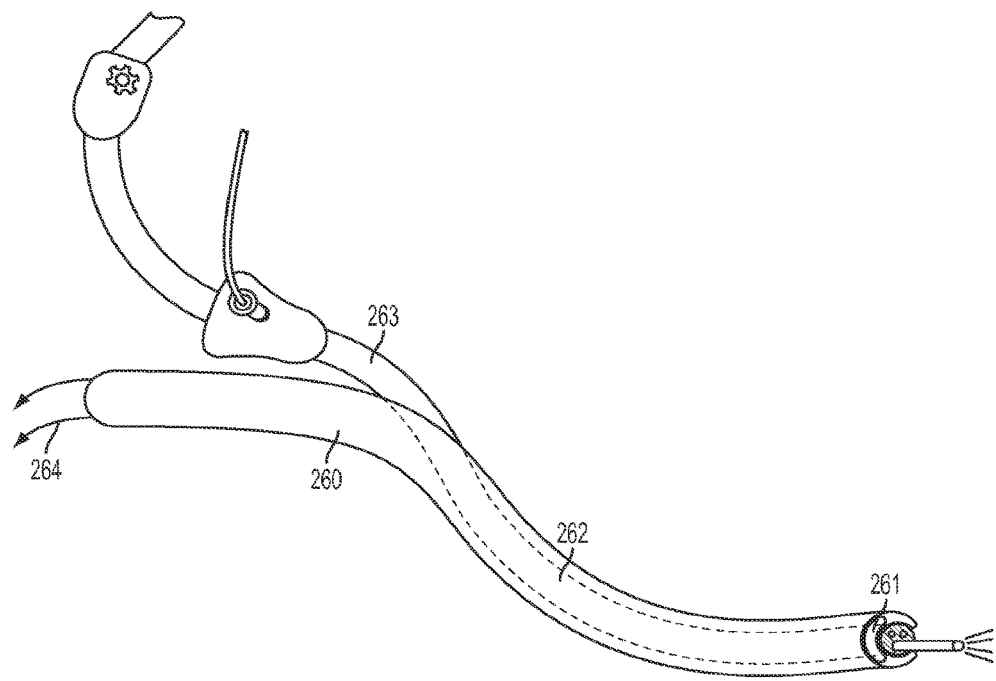
FIG. 17 is a perspective view of the vent tube and scope shown in FIG. 16.

Alternatively, the controlled pressure and pulsing, coupled with careful control of catheter diameter and length helps further deliver controlled flow of volume over time that is consistent with the cryogenic property of the fluid being delivered. Dual phase fluid flow is achieved out of the catheter distal tip and maintained constantly via the equilibrium that the system achieves after pre-cool and after the catheter achieves a cold temperature. The range of dual phase fluid cryogen delivery out of a cryogen catheter with this system can range from 5 LPM to 50 LPM (once it all expands into gas). The diameter of the area through which gas vents passively must be adequate to ensure distention does not occur. Passive venting may be used with a vent tube when spraying proximal to a resistor where the lumen is patent (open), or when the treatment area is open to atmospheric pressure (e.g., dermatological or open surgery). A lumen sizing device (e.g. stent sizer) may be used to measure the lumen to aid in selection of vent tube size. The greater the vent area, the lower the pressure. The vent tube can be a separate tube used strictly for venting gas and creates a round vent area. The vent tube can also provide an annular vent area where the scope passes through the center of the tube. FIG. 3 shows a comparison of annular and round vent area. FIGS. 4 and 5 show vent areas (mm$^2$) for different scope sizes and vent tube inner diameters (ID). The distal end of the passive venting tube should be placed in an unobstructed cavity near the procedure area if area is not sufficiently open to atmospheric pressure. If used, the proximal end of the passive venting tube should be positioned outside the body where the pressure is atmospheric. FIGS. 4 and 6 show maximum expected pressures during a 20-second spray using round or annular vent shape, respectively. In FIG. 17 the vent tube 260 takes the shape of sleeve with a lumen 261. Such sleeve 262 or grooved channel 262 can then be utilized to slip the scope 263 into it to allow for the scope insertion into the body cavity to be the placement mechanism. The vent tube is flexible enough that the functionality of the scope is not hindered. The tube ends with an open end 264 to vent to the atmosphere. FIGS. 13 and 14 show another version of the vent tube 266 with the sleeve rolled up 265 upon unpackaging, and a scope location opening 267, and a vent orifice 268. As shown in FIG. 15; it is unrolled over the scope shaft 269. And ready for use. FIG. 15 also shows the cryospray catheter 270 located out of the scope working channel. The vent hole may be of dual vent lumen or single vent lumen construction which in turn supports both passive and active (suction) venting.

Active Venting (Suction)

Active venting (suction) is the venting method in which the onboard suction is used to evacuate gas from the treatment area via the cryogen decompression tube 132. The suction is controlled by the physician through the use of a dual foot pedal (cryogen/suction) 101. Pressing the suction foot pedal 111 activates suction; pressing the suction foot pedal again de-activates suction (toggle action).

The on-board suction module is preferably mounted inside the lower front panel of the console. The suction control panel consists of a pump 168, control module, valve and sensor. The software set-up screen provides two user selectable levels of suction (normal, low). The front enclosure provides space for attaching a suction canister 169 and accessory tubing 167 One piece of pre-cut accessory tubing connects the suction canister to the console pump; another piece of pre-cut accessory tubing connects the suction canister to the decompression tubing. Electronic controls within the console verify adequate vacuum and allow the physician to control application of suction through the cryogen decompression tube using the foot pedal.

The prior art required the use of an external suction pump, while the console of the present invention has an integrated suction pump to improve overall consistency and provide control and self-checks. The present invention uses a normal vacuum setting to evacuate liquids that may accumulate in the treatment area or cryogen decompression tube in addition to removing the cryogen gas. The console of the present invention also has an additional, lower vacuum setting (50%) to allow the physician to pull less suction in certain situations (e.g., where flaccid lumen inhibits vision or movement). The integrated suction pump and sensor (32 lpm) improves consistency, suction flow, suction flexibility robustness relative to prior art external suction pump and gauge (25 lpm).

Spray Kit

The spray kit consists of a carton of five (5) sterile, single-use catheters with introducers in individual pouches and a carton of five (5) sterile, single-use CDTs with associated tubing in individual pouches. Each carton within a spray kit contains the instructions for use.

Catheter

The catheter is designed to transport liquid nitrogen from the console to the patient treatment site. The catheter contains (1) a bayonet and hub for attachment to the console at its proximal end, (2) a layered polyimide and stainless steel braided shaft to minimize kinking and breaking, (3) insulation to protect the user from cold, (4) a strain relief to help prevent kinking when torqued by users and (5) an atraumatic tip at its distal end to prevent damage to tissue. The laminated construction and braided material provides additional strength and flexibility, allowing the physician to retroflex the catheter during a treatment procedure, if needed. The catheter pouch contains an RFID tag that the user scans prior to use to prevent reuse and track disposable information. The catheter pouch also contains an introducer that provides reinforcement for the catheter and helps prevent kinking during use and when placing the catheter into the scope. The catheter is packaged in a protective tube to prevent damage during shipping.

The delivery catheter is comprised of three layers of flexible polyimide, surrounded by a stainless steel braid, which is in turn coated with an outer layer later of PEBAX®. It was discovered that that extrusion of PEBAX® over the stainless steel braid allows the PEBAX® to wick through the pitch of the steel braid, helping to prevent kinking, breaking, or delamination during retroflex of the catheter. The PEBAX® also provides a desirable balance between hardness—important for smooth sliding of the catheter and general toughness, and softness, which is important for some degree of tackiness which allows the user to feel the movement of the catheter in the scope. The pitch of the stainless steel braid is configured to be fine enough to afford the required strength, not thick enough to allow the PEBAX® to wick through. The distal end of the catheter is provided with an atraumatic tip comprised only of PEBAX®, in the shape of a bullnose. This novel construction allows for retroflex of the catheter without kinking, breaking, or delamination of the catheter. For the purposes of this invention, retroflex is used to refer to the ability of a catheter to bend or turn approximately 180° about a radius of curvature of 1 inch or less. This is useful so that when the catheter is introduced into, for example, the stomach via the esophagus, the catheter can be turned approximately 180° in order to treat the roof of the stomach.

Figure 18:
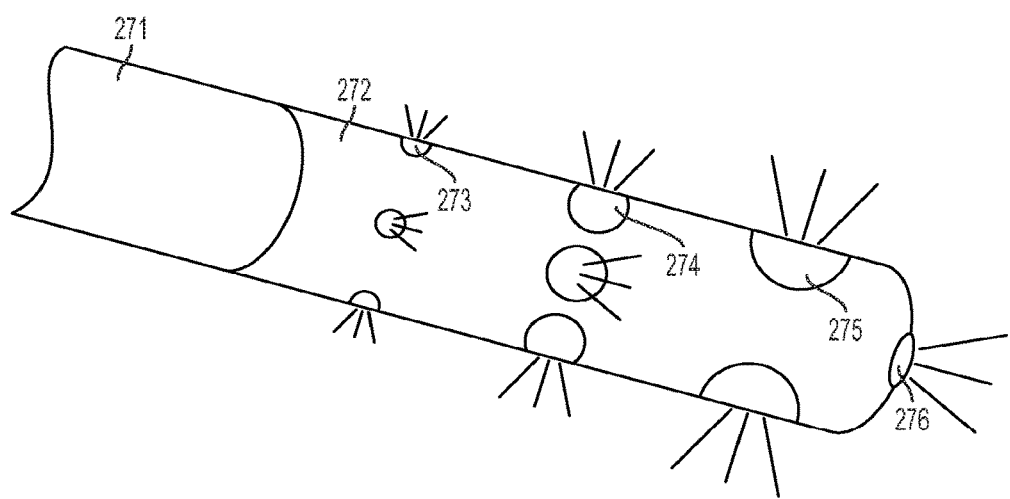
FIG. 18 is a side view of an embodiment of a catheter tip according to the invention.

In alternate embodiments the distal end of the catheter may be a preformed plastic tip (typically PEBAX®) with a specific geometry that allows for specific spray patterns other than those coming out of the catheter shaft end (aka. straight spray). FIG. 18 demonstrates a catheter 271 with a spray pattern tip 272 that shows holes 273, 274, 275 of different sizes at different distance positions that allow for gradual spray across a specific distance of the catheter shaft 271. The hole patterns 273, 274, 275 may have dimensions that are between 0.015" to 0.050" in diameter. In this illustration, the hole at the distal end of the catheter 276 for straight spray may or may not be there and it is of a diameter that is also different from the rest. This diameter of this hole 276 may have a range or 0.020" to 0.085 inches. The construction of this tip may be achieved via drilling of the different hole sizes, fusing or adhering a preformed and predrilled tip or insert molded via micromolding techniques.

Figure 19:
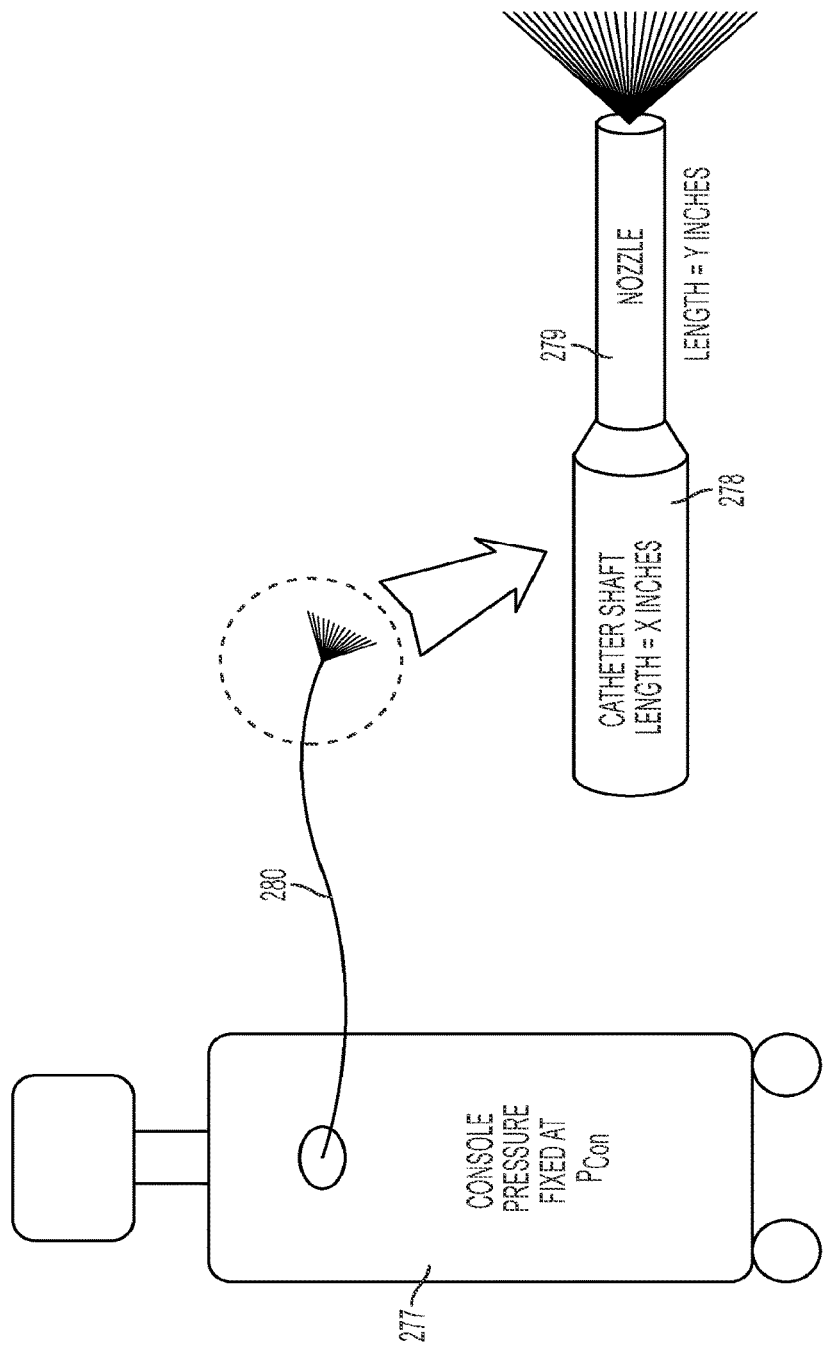
FIG. 19 is an illustration of an embodiment of the invention in which the catheter tip is fitted with a nozzle.

In yet another alternate embodiment, the control of the cryospray is achieved through a nozzle flow created by shafts of a certain length and diameter size. FIG. 19 demonstrates how the Pressure of the console 277 may remain constant, but the combination of catheter shaft 278 and nozzle 279 are used to throttle the output flow at the distal end of the catheter 280 with a specific output flow. The nozzle 279 length can have a range of 0.050" to 48 inches in length and an inner diameter of 0.030 to 0.080 inches. Likewise the catheter shaft 278 of this construction can have a range of 1.5 inches to 90 inches when coupled with the nozzle construction. The catheter shaft can have an inner diameter range of 0.30 to 0.125 inches.

Another embodiment to be mentioned contains a catheter with a temperature probe attached to the distal end of the catheter. This is achieved by laying at least two wires longitudinally or in a coil pattern prior to the outer layer of polymer laminated onto the catheter outer layer. If the wires are thermocouple wires, then they can be terminated into a thermocouple. Alternatively, a cryogenic thermistor can be attached to the distal end of the catheter. Such thermistor can then be encapsulated via conductive epoxy and an FEP heat shrink to sleeve it. Then the thermistor can be used to monitor both the temperature at the end of the catheter tip as well as the treatment area for both freezing and thawing temperature monitoring.

Figure 20:
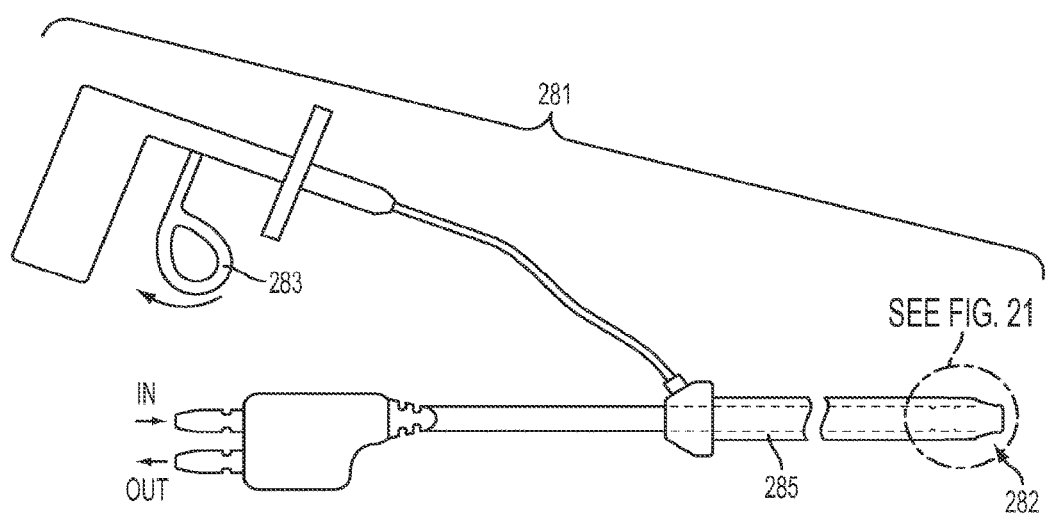
FIG. 20 shows a cryogen recirculating catheter according to an embodiment of the invention.

One more alternative embodiment that we wish to discuss is the invention of a dual lumen of lumen within lumen catheter construction. Such construction results in a cryospray catheter that can now be precooled via the recirculation of fluid all the way to its distal end. FIG. 20 describes such method. The precooling is either achieved by the console control or the user's input command (like via a foot pedal). The cryospray catheter 281 contains a valve or shutter 282 that is then engaged either via the console control or the user. FIG. 20 describes the trigger type mechanism 283 that is engaged by the user for the duration of the spray to the treatment site. The mechanism 283 can be spring loaded to allow it to retrieve to the close position after treatment time is done. The valve is mechanically connected remotely to the trigger mechanism 283 via an engagement wire 284 running along the length of the catheter shaft 285. The wire 284 is connected to a sleeve sliding sleeve so that when the trigger is engaged the sleeve slides back and opens up the elastomeric diaphragm as shown retracted in dashed lines. A failsafe to the valve 282 opening and closing is the user can depress the console flow control that stops the recirculation along the catheter shaft 285 if the mechanical trigger fails to immediately retract due to freezing issues. The catheter shaft consists of dual lumens with an input and an output port for the path of recirculation.

Figure 21:
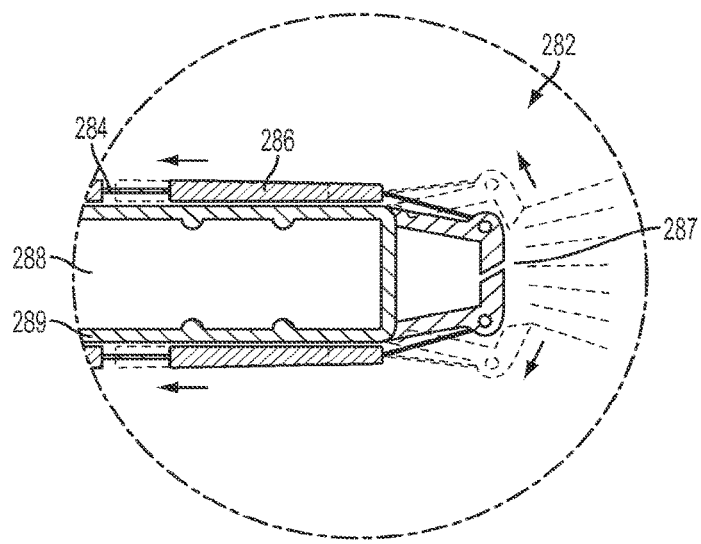
FIG. 21 is a closeup of the distal tip of the catheter shown in FIG. 20.

In FIG. 21, the recirculation path is shown via an inner lumen 288 that is surrounded by an outer lumen 289 which returns the dual phase fluid flow back to the console for recollection. Holes on the inner lumen 288 allow for this to occur.

Cryogen Decompression Tube

The cryogen decompression tube 132 aids evacuation of nitrogen gas from the treatment site. The cryogen decompression tube connects via supplied accessory connection tubing 167 to a disposable suction canister 169 on the front of the console. The dual lumen cryogen decompression tube are coupled by ports that provide both active (to the suction pump) and passive (direct to ambient) vent paths.

Figure 22:
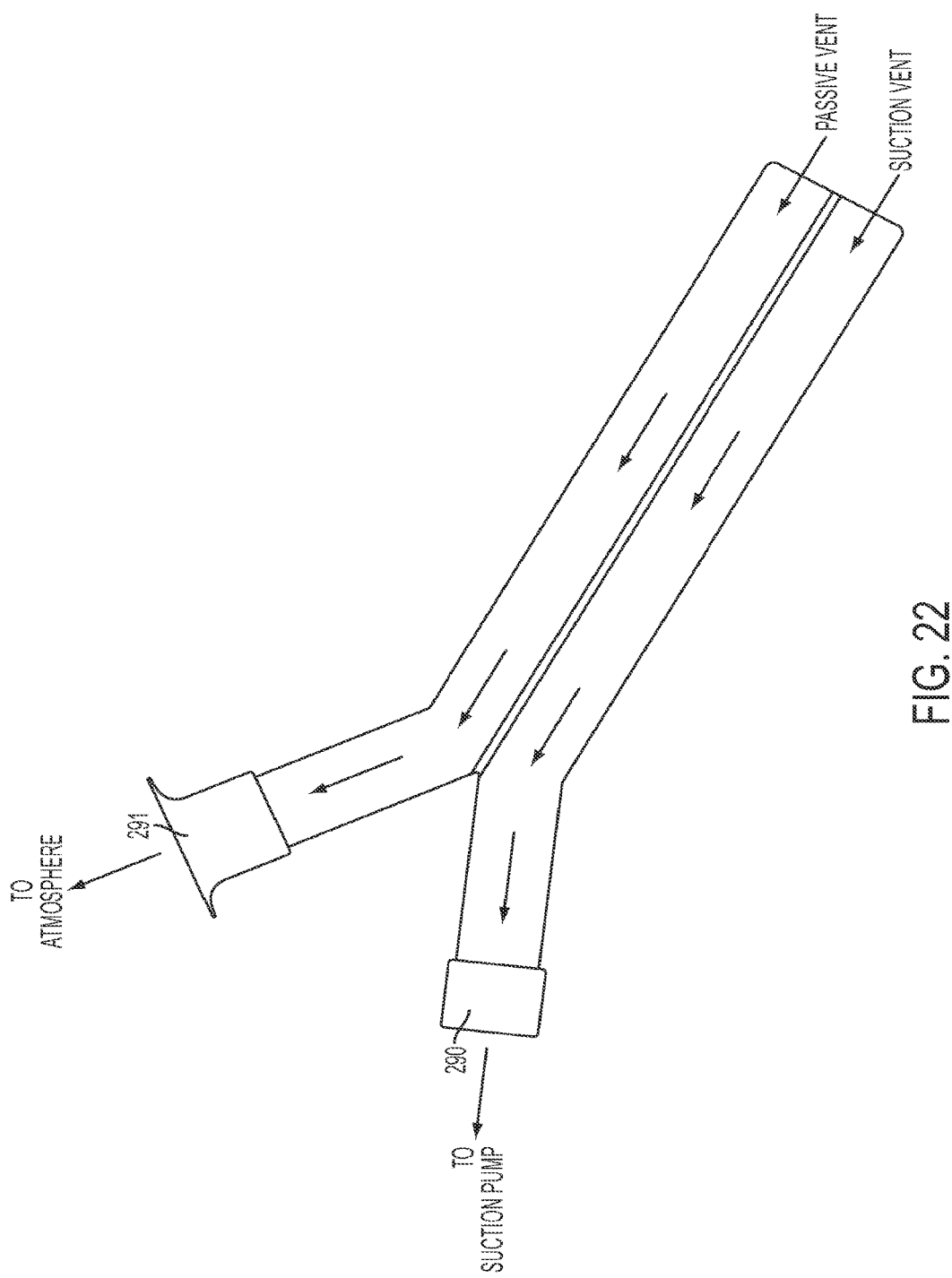
FIG. 22 is a sideview of a dual lumen vent tube according to an embodiment of the invention.

The dual lumen cryodecompression tube may be of the form on FIG. 22, where each lumen is independently vented to either a suction pump tube connection or a passive open air connection 291. The passive venting may serve the function of vent during cryospray, but also the function of working channel to supplement the absence of a working channel if the catheter is inserted into the working channel of the scope. Such working channel can be used for tissue manipulation, forceps, biopsy, among other uses.

Scan/RFID

Spray kit usage is tracked by scanning a Radio Frequency Identification (RFID) tag on the catheter packaging. The RFID reader 306 is mounted on the right side of the console. When a valid spray kit is detected, the associated indicators on the set up screen are updated and a three hour timer is started and constantly visible to the user for monitoring of procedure time. In the preferred embodiment the RFID tag is scanned by the user upon connection of the catheter, and the catheter type logged on the system. In an alternate embodiment such RFID tag may be located on the device itself, instead of the packaging and recognized upon catheter connection by the user. Such connection may identify catheter type, spray flow output, and provide the pressure setting value for the system to adjust to for treatment.

Control/Electronics Panel

The control panel is located in the top upper section of the console and includes the following: auxiliary panel (pressure port 308, thermocouple input port 310 and digital input ports 312), emergency stop 314, USB port, catheter interface 318 and transfer interface, including external fill port 166. The catheter port on the console of the present invention has spring-loaded capture pins for good connection and good tactical feel on insert and removal.

The electronics panel houses the compact data acquisition (cDAQ) controller, the level sense signal conditioner, the auxiliary pressure sensor, the interface board, the heater relay, the power supply and the power supply filter. The cDAQ controller contains removable DAQ modules that measure and output various signals and controls to and from the console. All signals and controls in the console are routed through an interface/interconnect board. The console of the present invention uses a universal medical grade power supply that powers all internal operations using 24 volts through the interface/interconnect board. Power from the 24 VDC medical grade power supply is distributed to all console components through the interface board.

User Interface/Platform

The improved system of the present invention utilizes a graphical user interface (GUI) deployed on a touch panel. The software is comprised of six main application codes that govern operation of the system: Home, Fill, Test, Run (Procedure Data and Service.

The Home module provides the central menu and access to the five application modules. Three (3) buttons located in the center of the Home screen allow access to the three main modules: Fill, Test and Run. Data and Service buttons are normally hidden; however, pressing the CSA logo makes them visible. Service is password protected allowing only authorized CSA personnel access. The module application codes are accessed by selecting the applicable button from the Home screen.

The Fill module implements a semi-automatic fill process that (1) verifies the fill hose is connected before proceeding, (2) controls applicable valves required for filling the tank, (3) displays the real time tank level and (4) automatically shuts off when the tank is full.

The console of the present invention includes a semi-automated fill process accessed from the front of the console that provides graphical information to monitor the fill process. The prior art is a manual process conducted at the rear of the console that does not include a visual display during fill.

The test module implements an automatic built-in test (BIT) when powering up the console or when selected by the user. The BIT checks each hardware module and verifies performance of the system prior to entering the procedure code (i.e., Run button). Upon completion, the BIT automatically returns to the Home module. Once the BIT is completed, the Run button is enabled for entrance into Run Mode. If the BIT fails, a status indicator on the Home screen alerts the user of the required action and disables the Run button. The console of the present invention allows the user to view both quantitative and pass/fail results for each test as they are completed as well as an overall result.

The procedure application module (Run button) controls the thermal, timing and suction functions and is used during the treatment of patients. When the Run button is pressed, the user can select from a set-up screen or a run screen. The set-up screen monitors key system parameters (scan, tank level, pressure, and thermal) with color coded text indicators to indicate operating states (green ready, red not ready). The set-up screen also contains controls for selecting cryogen flow (normal/low), suction (normal/low), and sound volume (normal/low). The run screen provides inputs to set and control the timer, precool and defrost. The run screen also provides color coded procedure, suction state/warning indicators and auxiliary pressure indicators.

The console of the present invention has optional lower cryogen flow and suction setting. The system of the present invention displays additional information regarding the system status (e.g., tank level, tank pressure, precool, cryogen state, suction/venting state).

The Data module provides the ability for the user to view and download log files through a drop down menu. There are a total of six (6) logs that are visible to the user (fill, test, procedure, system, error, and service) to view relevant details. Log files may be downloaded to a USB drive for off-line viewing and aid in service support.

The console of the present invention provides the ability for the user to read and display log files directly on the panel PC, improving serviceability and ease-of-use. The prior art has independent service software to extract and view the data logs.

Remote Control

Various timer controls found on the main console are duplicated on a hand-held remote control: site increment/decrement, cycle increment/decrement and timer start/stop and clear. Large blue buttons on a white background provide desired optical contrast and visibility in low light environments and good tactical feedback. Communication uses the IEEE 802.15.4 communication standard and chips in both the console and remote control contain a unique serial number that is used to establish a one-to-one connection.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A mobile cryosurgical apparatus for cryogenic spray ablation comprising:
    a cryogen tank for storing cryogen under pressure;
    a cryogen pressure measuring device configured to measure a pressure of the cryogen tank;
    a cryogen pressure maintenance system configured to monitor the pressure of the cryogen tank via the cryogen pressure measuring device and control the pressure of the cryogen in the cryogen tank during use of the mobile cryosurgical apparatus;
    a cryogen level measuring device configured to measure a cryogen level in the cryogen tank;
    a cryogen tank fill system for filling the cryogen tank with cryogen;
    a catheter attachment apparatus for attaching a cryogen delivery catheter to the mobile cryosurgical apparatus;
    a catheter pre-cool system for precooling the cryogen delivery catheter;
    a catheter defrost system for defrosting the cryogen delivery catheter;
    an on-board suction system configured to evacuate gas from a treatment area;
    a user-control system for user-control of cryogen flow and application of suction via the on-board suction system;
    an on-board computer screen for interacting with the mobile cryosurgical apparatus; and
    an on-board control system comprising a non-transitory computer readable medium containing computer readable instructions for monitoring and adjusting cryogen pressure via the cryogen pressure maintenance system controlling a cryogen tank fill operation via the cryogen tank fill system running pre-procedure system checks, controlling catheter pre-cool and defrost using the catheter pre-cool system and the catheter defrost system, respectively, and controlling thermal, timing and suction functions at least in part using the user-control system during user treatment of patients.

2. The mobile cryosurgical apparatus according to claim 1, wherein the cryogen delivery catheter is configured to deliver low pressure cryogen spray from the mobile cryosurgical apparatus to a treatment area through an endoscope.

3. The mobile cryosurgical apparatus according to claim 2, wherein the cryogen delivery catheter comprises an inner tube of extruded polyimide, a layer of braided stainless steel over the extruded polyimide, and a layer of PEBAX® extruded over the braided stainless steel, wherein the PEBAX® extends through the stainless steel braid to at least partially contact the polyimide layer, said cryogen delivery catheter further comprising a blunted tip with PEBAX®; wherein said catheter is capable of retroflex during use, without kinking, breakage or delamination.

4. The mobile cryosurgical apparatus according to claim 1, further comprising a dual lumen cryogen decompression tube with a passive lumen and a suction lumen configured to allow simultaneous passive venting and active suction through the passive lumen and suction lumen from a treatment area while preventing over-suction during non-treatment intervals.

5. The mobile cryosurgical apparatus according to claim 1, wherein said user-control system for user-control of cryogen flow and application of suction comprises a dual pedal control device including a first pedal communicatively connected to valving in the apparatus, with a pressed state and an un-pressed state for controlling the delivery of cryogen from said cryogen tank, the pressed state opening the valving, and the released state closing the valving; and
    a second pedal configured for connection to a vacuum source, with a first pressed state configured to activate suction from said on-board suction system, and a second pressed state configured to shut off the suction system.

6. The mobile cryosurgical apparatus according to claim 1, wherein said cryogen pressure monitoring system and said cryogen pressure maintenance system are configured to be active during cryospray treatment of a patient and comprise an electronic pressure sensor configured to monitor the pressure of the cryogen tank, an electronic pressure build solenoid configured to respond to instructions from said on-board control system to selectively allow flow of liquid cryogen from a lower portion of said cryogen tank to an upper portion of said cryogen tank in order to increase the pressure thereof as necessary, and an electronic solenoid vent under control of said on-board control system to selectively vent cryogen from said cryogen tank to decrease the pressure thereof as necessary.

7. The mobile cryosurgical apparatus according to claim 1, wherein said cryogen level monitoring system comprises a three-point cryogen tank support system; an electronic load cell located at one point of the three point cryogen tank support system and configured to determine the load borne by the support at the one point; and electronics for communicating the load recorded to the on-board control system.

8. The mobile cryosurgical apparatus according to claim 1, wherein said cryogen fill system monitors the level of cryogen in the cryogen tank level and sends instructions to an electronic cryogen fill solenoid to close off flow of cryogen into said cryogen tank and automatically vents a supply hose.

9. The mobile cryosurgical apparatus according to claim 1, further comprising a user input interface that permits the user to select the delivery of cryogen at a plurality of discrete pressures.

10. The mobile cryosurgical apparatus according to claim 1, further comprising a user input interface that permits the user to select the use of passive venting only, or active venting at a plurality of discrete suction powers.

11. The mobile cryosurgical apparatus according to claim 1, wherein the catheter pre-cool system is set to automatic by the user and prevents the flow of cryogen into a delivery catheter until cryogen delivery components internal to the cryosurgical apparatus reach a specified temperature.

* * * * *